(12) United States Patent
Bristow

(10) Patent No.: US 7,744,883 B2
(45) Date of Patent: Jun. 29, 2010

(54) METHOD FOR REDUCING THE NUMBER OF UNWANTED MOLECULES IN BLOOD

(75) Inventor: Duke K Bristow, Los Angeles, CA (US)

(73) Assignee: Advanced Extravascular Systems, Inc., Sherman Oaks, CA (US)

( * ) Notice: Subject to any disclaimer, the term of this patent is extended or adjusted under 35 U.S.C. 154(b) by 752 days.

(21) Appl. No.: 10/778,662

(22) Filed: Feb. 13, 2004

(65) Prior Publication Data

US 2004/0161736 A1    Aug. 19, 2004

Related U.S. Application Data

(63) Continuation of application No. 09/566,510, filed on May 8, 2000, now abandoned.

(51) Int. Cl.
A61M 1/34 (2006.01)
(52) U.S. Cl. .................. 424/140.1; 604/4.01; 604/5.01; 604/6.01; 604/6.09; 435/2
(58) Field of Classification Search ........................ None
See application file for complete search history.

(56) References Cited

U.S. PATENT DOCUMENTS

| 4,247,393 | A |  | 1/1981 | Wallace |
| 4,375,414 | A |  | 3/1983 | Strahilevitz |
| 4,576,928 | A |  | 3/1986 | Tani et al. |
| 4,581,141 | A |  | 4/1986 | Ash |
| 4,714,556 | A |  | 12/1987 | Ambrus et al. |
| 4,770,774 | A |  | 9/1988 | Ida et al. |
| 4,787,974 | A |  | 11/1988 | Ambrus et al. |
| 5,061,237 | A |  | 10/1991 | Gessler et al. |
| 5,753,227 | A |  | 5/1998 | Strahilevitz |
| 5,871,649 | A |  | 2/1999 | Ofsthun et al. |
| 5,880,270 | A |  | 3/1999 | Berninger et al. |
| 6,080,404 | A | * | 6/2000 | Branham et al. ......... 424/140.1 |

OTHER PUBLICATIONS

Higgins et al, "Antibody Removal Therapy in Transplantation" Transplantation Reviews, 1995, vol. 9, No. 4, pp. 177-199.*
Callegaro et al., "Applications of Bioreactors in Medicine," Int. J. Artificial Organs 6:107-110 (1983).
Bensinger et al., "Whole Blood Immunoadsorption of anti-A and anti-B antibodies," VoxSanguinis 48(6): 357-61 (1985).
Huffman et al., Industrial & Engineering Chemistry Process and Development 14(2): 166-170 (1975) Abstract.

* cited by examiner

*Primary Examiner*—Allison M Ford
(74) *Attorney, Agent, or Firm*—William W. Haefliger

(57) ABSTRACT

The present invention provides a method, and resulting product, for the removal of unwanted molecules from a host's blood using a one-step procedure. The unwanted molecules may be anti-A blood protein and/or anti-B blood protein antibodies that would otherwise cause host rejection of transplanted organs or tissues from a source having a different ABO blood type. The unwanted molecules may also be excess antibodies, or virions, present in a diseased host.

23 Claims, 5 Drawing Sheets

METHOD FOR REDUCING THE NUMBER OF UNWANTED MOLECULES IN BLOOD

This application is a Continuation of Ser. No. 09/566,510, filed May 8, 2000, now abandoned which is incorporated herein by reference.

FIELD OF INVENTION

This invention relates to technology for reducing the presence of unwanted molecules, including those related to disease states and those involved in rejection of transplanted organs and tissue, a host's blood. In particular, the invention discloses a method and a system for reducing the presence of unwanted molecules, such as anti-A and anti-B antibodies, by a one step removal process. It also discloses blood substantially of unwanted antibodies, antigens, and the like.

BACKGROUND OF THE INVENTION

Traditionally, organ or tissue transplantation requires ABO blood type compatibility in order to prevent graft rejection. Normally, the host's blood contains circulating antibodies against foreign blood type antigens. Transplantation across these ABO blood groups leads to hyperacute rejection of the graft within the first 24 hours (Kuby J: Immunology. New York, W.H. Freeman and Company, 1997). Circulating antibodies bind to blood antigens present in red blood cells, epithelial cells and endothelial cells found in the graft organ or tissue. These antibody-antigen complexes activate the complement system of the host, resulting in infiltration of neutrophils into the graft organ or tissue. The neutrophils release lytic enzymes that destroy the graft endothelial cells, providing a surface of injured tissue to which platelets can adhere. Massive blood clots form within the capillaries, and this whole inflammatory reaction prevents vascularization.

Current treatments to reduce rejection include administering a regimen of immunosuppressant drugs before and after the transplantation surgery. Studies have been performed on methods that remove antibodies specific to ABO antigens. These methods have also shown beneficial effects in reducing hyperacute rejection of the transplanted organ or tissue. These methods are important because they may lead to a method which will relax the requirement of donor/recipient ABO compatibility, which in turn can greatly expand both the living donor and cadaver organ or tissue pools.

Current techniques to remove the ABO antibodies include plasma exchange combined with intravenous administration of soluble ABO antigens (Alexandre G P J, et al., Neth J Med, 28:231-234, 1985); separating plasma from the whole blood by either centrifugation or double filtration plasmapheresis (DFPP) followed by immunoadsorption using concentrated red blood cells (Slapak M, et al., Transplantation 31:4-7, 1981); and DFPP followed by column immunoadsorption of anti-A and B antibody using A and B antigen bound to silica beads (Tanabe K, et al., Transplantation Proceedings, 27(1) 1020-1023, 1995).

These prior art methods have serious problems which have prevented their adoption as the standard of care. First, there is the risk of infection. Because plasma exchange by centrifugation requires replacement by plasma protein solution, risk of viral transmission is present. Moreover, these techniques described above involve first separation of plasma from whole blood then an additional procedure to remove ABO antibodies from the plasma. Separated plasma can then be stripped of pre-existing anti-A and B antibodies by immunoadsorption with ABO antigens linked to silica beads on a column.

A study on renal transplantation has shown that ABO-incompatible grafted patients who received one or two sessions of DFPP and three or four sessions of column immunoadsorption showed no significant difference in survival rates when compared to patients who received an ABO compatible graft (Tanabe, supra). Additionally, one case has been reported in which hyperacute rejection following accidental ABO-incompatible renal transplant was reversed using plasmapheresis followed by immunoadsorption with red blood cells (Slapak, supra).

SUMMARY OF THE INVENTION

This invention provides a method and system for reduction of a host's rejection of a non-autologous organ or tissue transplant caused by the presence of foreign antigens in and on the organ or tissue. This is accomplished by providing a method for one-step removal of antibodies in the host's blood that are directed to the foreign antigens. For example, cross-ABO rejection can be eliminated by removing anti-A and/or anti-B antibodies, in one step, from the host's blood. This is done by moving blood extracted from the host along a pathway, which is optionally semi-permeable, having antigen specific to the antibodies, such as antigens that bind to anti-A and anti-B antibodies, attached to the pathway, and returning the blood to the host internal circulation.

In another embodiment, this invention provides a method for removing, in one step, excess antibodies, such as are present in certain disease states, from a host's blood by moving the blood extracted from the host on a pathway, optionally semi-permeable, having antigens or anti-antibodies specific to the unwanted antibodies immobilized in the pathway, and returning the blood to the host's internal circulation.

In yet another embodiment, unwanted antigen is removed from a host's blood in one step by moving the blood extracted from the host on a pathway, optionally semi-permeable, having antibodies specific to the antigen immobilized in the pathway, and returning the blood to the host's internal circulation.

In another embodiment, this invention provides blood that is substantially free of undesired molecules, such as anti-A and anti-B antibodies, wherein A and B are blood type antigens. The undesired molecules may also be antibodies associated with a disease state comprising an excess of antibodies in the blood, virions, and other undesired antigens.

In the preferred practice of the invention, a hollow fiber has attached A and B blood type antigens that are capable of sequestering the antibodies specific to A and B antigens from the flowing blood. In another preferred practice of the invention, the hollow fiber with attached antigen has semi-permeable pores that allow dialysis or plasmapheresis of the blood to occur at the same time. In a further preferred practice of the invention, the hollow fiber is coupled to a plurality of perpendicular membranes having attached antigen. Alternatively, this plurality of membranes can also be longitudinally placed inside and along the length of the fiber. In the most preferred embodiment, the antigens are attached to the wall of the hollow fiber. In further practice of the invention, the hollow fiber can be replaced by a flat membrane in a closed container that the blood can flow along or pass through. In this embodiment, an optional semipermeable membrane is present to divide the flowing blood from a slurry that will induce the blood components, such as antibodies, to exchange across the membrane.

The invention also provides a method to increase the organ or tissue pools available for transplant by removing in one step, from the host's blood, antibodies specific to foreign antigens present in the transplanted organ or tissue The invention also provides a one-step system for removing antibodies to specific antigens from blood in one step.

The invention also provides a one-step system for harvesting antibodies to specific antigens from blood.

In another embodiment, the present invention provides circulating blood that is substantially free of unwanted molecules, wherein these molecules are capable of binding, either specifically or non-specifically, to a binding partner capable of being immobilized on a pathway. In particular, this invention provides circulating blood that is substantially free of anti-A blood protein and anti-B blood protein antibodies.

DETAILED DESCRIPTION OF THE PREFERRED EMBODIMENTS

This invention provides a method and a system for one step removal, from the host's blood, of antibody specific to foreign antigens present in a transplanted organ or tissue. This is done by moving blood extracted from the host along an enclosed pathway such as a hollow fiber or flat dialyzer comprising bound or immobilized specific antigen, and returning the blood to the host internal circulation. The blood components are dialyzed across the membrane of the pathway, while at the same time antibodies are removed from the blood through binding to the immobilized antigen. The binding can be specific, as when the antigens are chosen to be the specific binding partners of the antibodies, or nonspecific, as when a general binding molecule such as protein A or protein G is used to bind the antibodies.

The antibodies, along with undesired small molecules (urea, creatinine, ammonia), are thus removed from the host's blood. Additionally, these antibodies can be collected by releasing them from their binding partners.

Expanding on this technique, the invention also provides a means for removing other unwanted molecules from a host's blood. For example, virions present in the blood due to a viral infection of the host can be removed by utilizing immobilized antibodies, either monoclonal or polyclonal, to the virion.

Materials
  Enclosed Pathway

The present invention comprises an enclosed pathway that allows the flow of blood and the trapping of one of the binding partners of a binding pair, such as an antibody and an antigen. The device can be made out of a variety of substances, including but not limited to nitrocellulose, cellulose, nylon, plastic, rubber, polyacrylamide, agarose, poly(vinylalcohol-co-ethylene), and the like, and combinations thereof. The material is preferably semi-permeable to allow the passage of small molecules out of the pathway.

The device can be formed in a variety of shapes, including but not limited to a flat dialyzer, a semi-permeable membrane, a semi-permeable hollow fiber, a coil, a dialysis membrane, a plasmapheresis filter, and multiples and combinations thereof.

Figure 1:
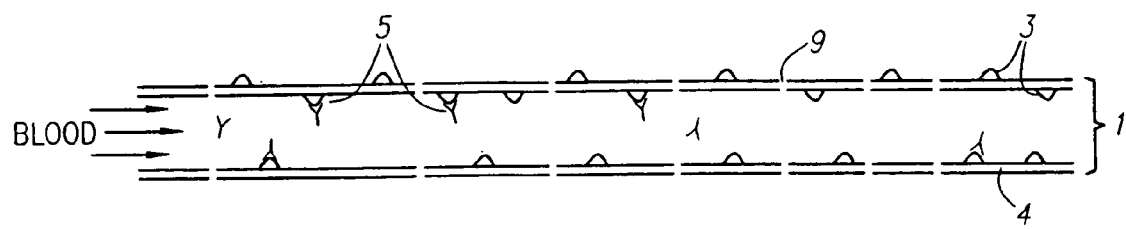
FIG. 1 is a longitudinal cross section view of an antibody removal system in accordance with a first embodiment of the present invention.

The preferred embodiment as shown in FIG. 1 uses a semi-permeable hollow fiber 1 for commercial dialysis with the antigen 3 attached to the wall 4 of the tubing with or without a linker molecule, for example PEG (polyethylene glycol), connecting one to the other. Use of dialysis membranes with attached antigen allows direct membrane immunoadsorption of the specific antibody 5 and plasmapheresis to occur at the same time.

Figure 2:
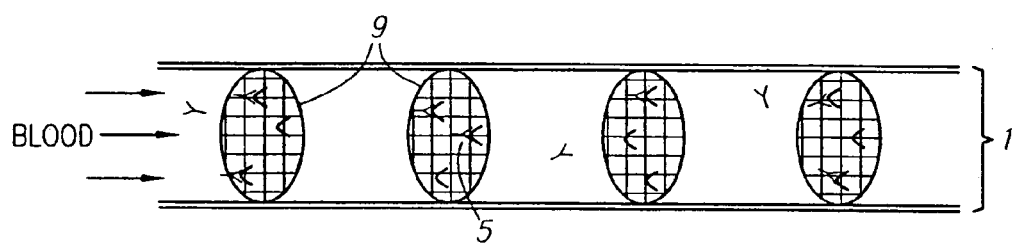
FIG. 2 is a longitudinal perspective section view of an antibody removal system in accordance with a second embodiment of the present invention.
Figure 3:
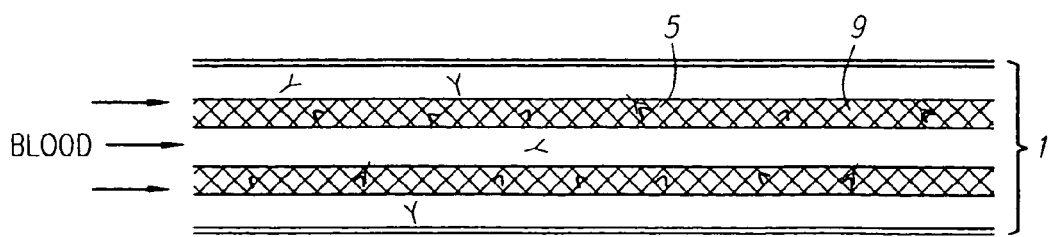
FIG. 3 is a longitudinal perspective section view of an antibody removal system in accordance with a third embodiment of the present invention.

Alternatively, other anchors for the immobilized binding partner can be used alone or in combination. For example, the hollow fiber 1 can have a plurality of flat membranes 9 that are placed longitudinally along the fiber length (FIG. 3) or perpendicular to the fiber (FIG. 2). The antigens 3 which are non-diffusively linked to this plurality of membranes 9, sequester the specific antibodies 5 from the blood as they pass along the hollow fiber 1. The membranes 9, preferably hi-flux membranes, allow blood cells and components to pass through so that no clogging occurs. The tubes themselves may be dimpled, twisted, or otherwise modified to increase mixing and binding of pathogen and antigen.

Figure 4:
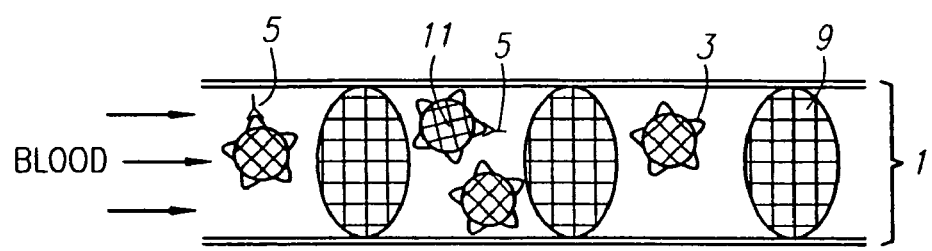
FIG. 4 is longitudinal perspective section view of an antibody removal system in accordance with a fourth embodiment of the present invention.

FIG. 4 shows another embodiment of the hollow fiber 1 where the antigens are linked to free floating permeable spheres 11 located inbetween the plurality of membranes 9. These spheres are trapped between the hi-flux membranes because of their size. The antigens 3 on the spheres 11 sequester the specific antibodies 5, thus removing them from the blood. Air or other non-toxic gas may be added at a lower elevation as small bubbles to further mixing and binding, and then the gas can be removed with a standard bubble trap at a higher elevation (not shown). The gas-induced mixing can occur on either the shell side or the tube (lumen) side.

Figure 5:
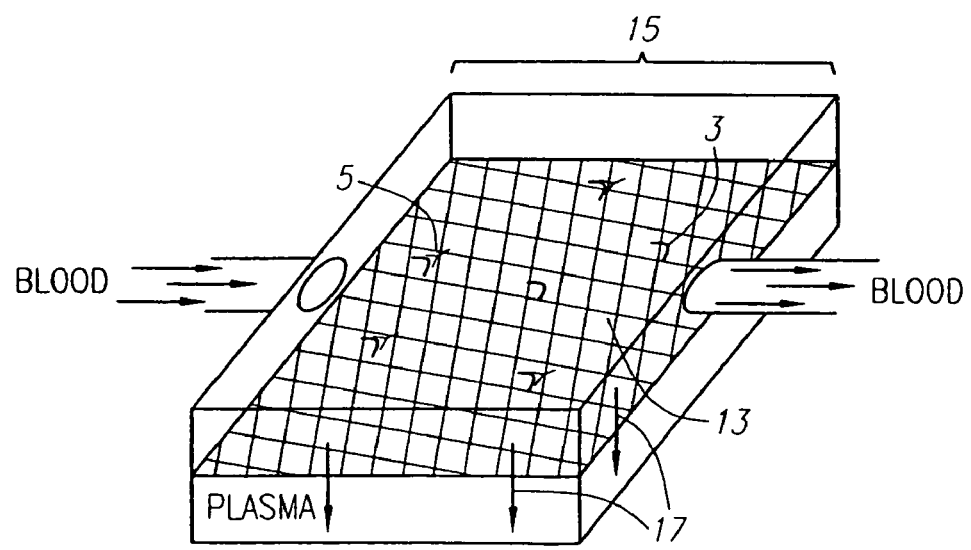
FIG. 5 is a top perspective view of an antibody removal system in accordance with a fifth embodiment of the present invention.

FIG. 5 shows another embodiment of the invention, where the antigens 3 are attached to flat semi-permeable membranes 13 of a flat plate dialyzer 15 instead of a hollow fiber. Blood plasma (as shown by downward arrows 17) passes through the membrane by convection but the specific antibodies are retained at the membrane. The blood travels along the pathway, continuously or temporarily interrupted, from left to right in the figure.

Binding Pair

This invention can be used with any binding pair, including but not limited to an antigen and an antibody, a receptor and ligand, an anti-antibody and an antibody, or binding portions of these molecules. By the term "binding portions" is meant any portion of the molecule that is capable of binding, either specifically or non-specifically, to a partner molecule so as either to be removed or to remove the binding partner from the blood.

In the preferred embodiment of the invention, the ABO blood group antigens are bound to the lumenal surface to remove their corresponding antibodies from blood. The antigen/antibody binding pair can be reversed wherein the antibody is bound to the luminal surface and the antigen is removed from the blood. Other antibodies, anti-antibodies, and antigens, such as major histocompatibility complex (MHC) molecules, or parts of these molecules, can be used to trap antibodies specific to these molecules. The antigen/antibody pair can further be replaced with any members of sets of binding pairs that would have specific affinities. Examples are ligands and receptors with some specificity to a pathogen.

Substance A and B antigens can be procured from Dade International in Switzerland (trade name: Neutr-AB). This mixture of Substance A and B antigen can be from a variety of natural sources, including but not limited to cows, pigs, horses and humans. These antigens, in their most reduced form trisaccharides, can also be made synthetically. A higher affinity for the antigen will exist when the antigen matches the original antigen to which the antibodies were produced. Likewise, the more purified the antigen is, the stronger the reaction.

Figure 6:
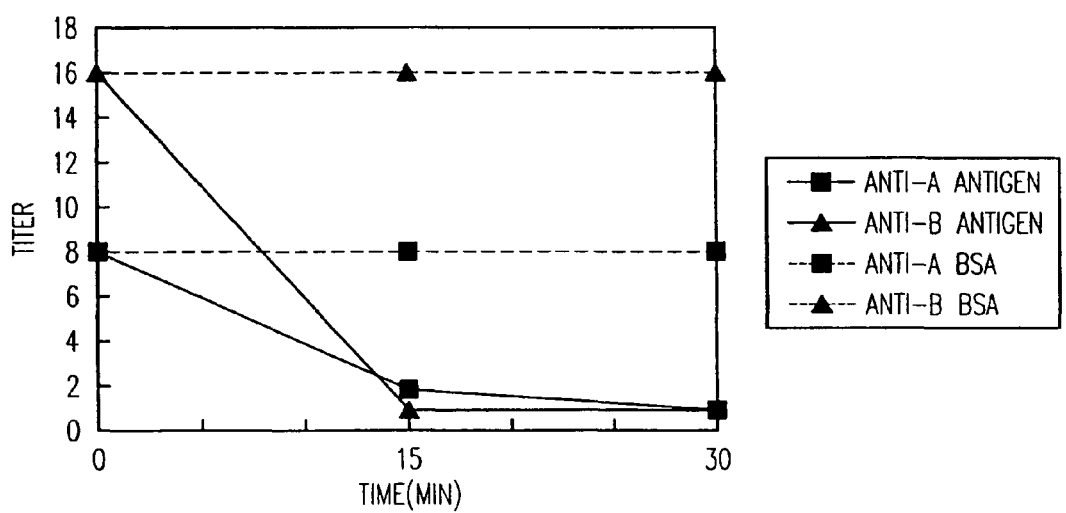
FIG. 6 shows the results of an assay using the method of this invention to remove anti-A and anti-B antibodies from blood.

The more antigen is present, immobilized directly on the lumenal surface or attached by a linking molecule in the enclosed pathway, the more specific antibody can be removed from the flowing blood. Likewise, the larger the surface area of the coated membrane, the higher the capacity for binding the desired antibody. For instance, 100 mg of antigen non-diffusively linked to a hollow fiber can significantly reduce the anti-A and anti-B titers of 300 to 400 ml of blood with from average to high titer. FIG. 6 shows the capacity of a modified hollow fiber to sequentially process 100 ml of banked human blood. Titer is determined by using a standard hemagglutination assay. This shows that membrane-bound antigen can specifically remove anti-A and anti-B antibodies, and that this removal takes place in the first 15 minutes of flow (about 3 passages of the blood over the membrane), regardless of original titer. Alternatively, one antigen type, such as Substance A or B, can be used.

Figure 7:
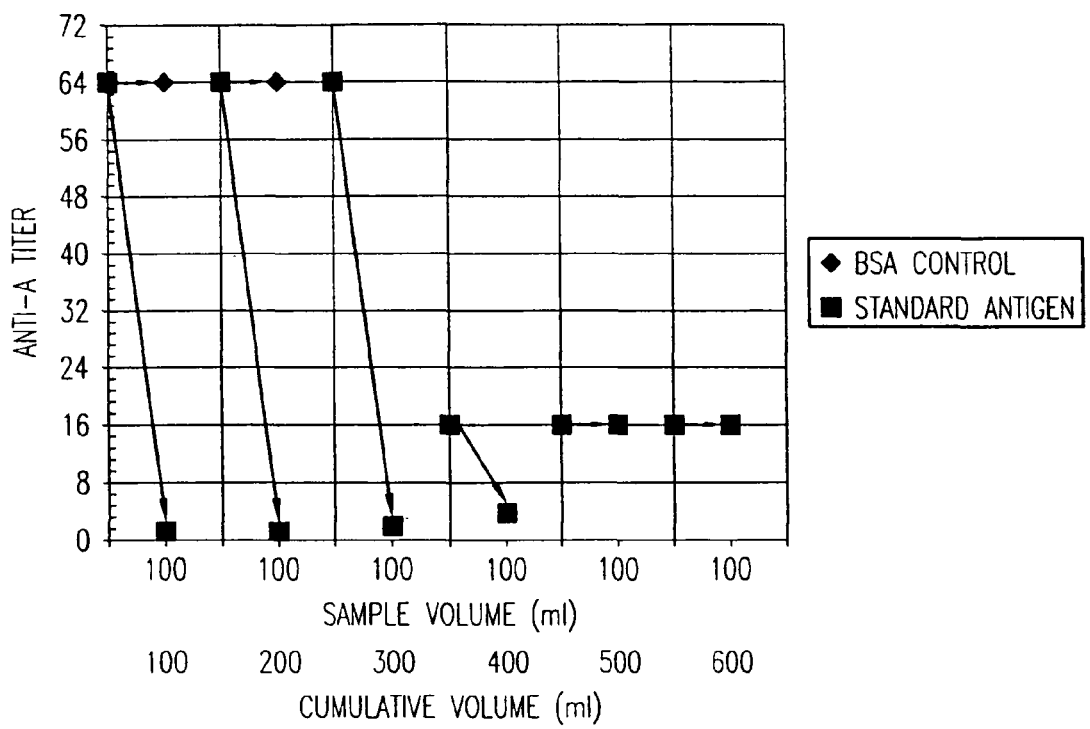
FIG. 7 shows the results of an assay using the method of this invention to remove anti-A antibodies from blood, showing the high capacity of the product.
Figure 8:
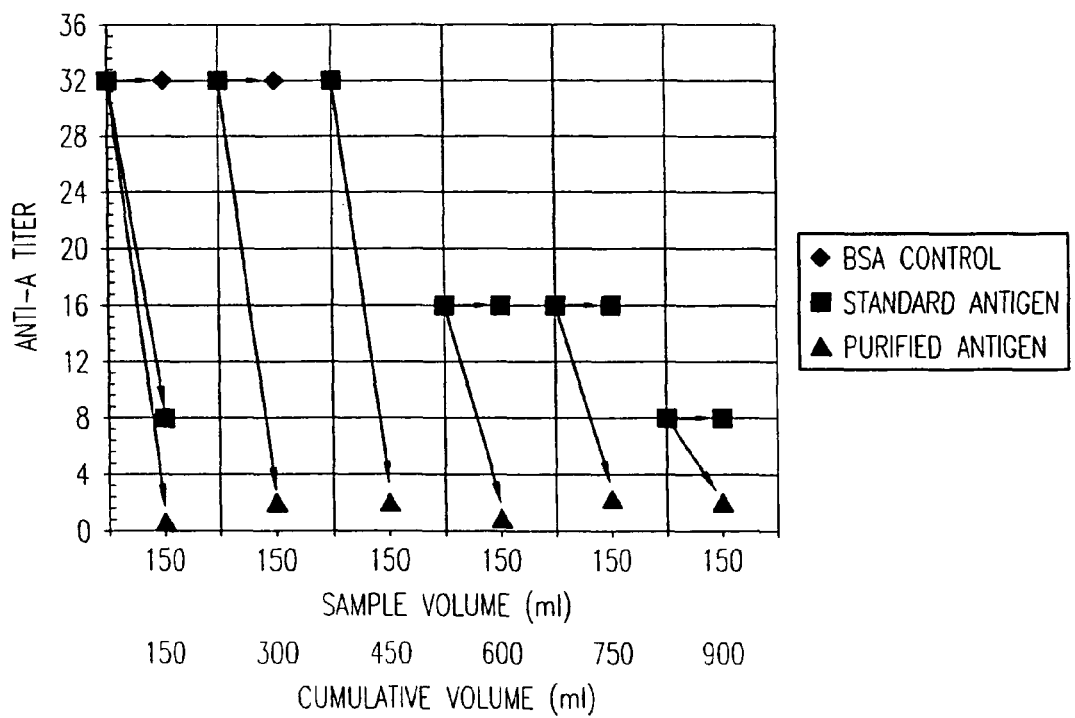
FIG. 8 shows the results of an assay using the method of this invention to remove anti-B antibodies from blood showing the high capacity of the product.

FIG. 7 shows the capacity of filters modified with A antigen for anti-A antibodies. FIG. 8 shows the same using B antigen for anti-B antibodies. Consecutive samples of blood were passed over the membrane until the membrane was saturated. At this point the titer of antibody in the blood samples no longer decreased upon passage over the membrane. The anti-A coated membrane had a capacity of around 300-400 ml. of average to high titer blood. The anti-B coated membrane had a capacity of around 600 ml.

Further purification of the standard antigens leads to at least a six fold increase in capacity to remove anti-A and anti-B antibodies per mg of antigen. Purification is achieved by removing components having molecular weight below 12,000 daltons from the commercially available antigen solution by dialysis. For example, the anti-A antibody capacity of a dialysis filter modified with approximately 40 mg of purified antigen reduced the anti-A titer of each of six 150 ml blood samples to 2 or below. The standard non-purified antigen-modified filter reduced the anti-A titer of the first sample from 32 to 8, and caused no titer reduction of the other five samples. The results were similar for the anti-B antibodies. Hence we expect that a dialysis filter modified with 100 mg of purified may be able to significantly reduce the anti-A and anti-B titers of 1.8 to 2.4 L of average to high titer blood.

Linking; of Binding. to the Enclosed Pathway

The antigen, antibody, binding pair member, ligand, or binding parts thereof, can be linked to the enclosed pathway by a variety of standard linking techniques, including but not limited to chemical modifications, covalent bonding, strong ionic or hydrogen bonding, use of a linker, etc. The preferred method uses standard cyanogen bromide (CNBr) linking which starts by treating the enclosed pathway with CNBr followed by incubation of the antigen and the modified pathway. The N-terminus of the antigen protein will covalently attach to the CNBr linker. Other compounds for treating the enclosed pathway include, but are not limited to, hydrogen peroxide, sodium periodate, epichlorohydrin, 1,4-butanedioldiglycidol ether, cyanuric chloride, carbonylkdiimidazole, substituted sulfonyl chloride, or fluoromethyl pyridinium salts, and antigen applied in the same way. Standard chemical linkers such as avidin and biotin can also be used.

Process

Filtration

Filtration of unwanted molecules from blood can be achieved using standard kidney dialysis type equipment which removes blood from one arm and returns it to the other. Alternatively, any pumping system connected to the patient at two sites, so as to draw blood from one site and return it to the other, will work. The blood is passed through the enclosed pathway having immobilized binding partners. The binding partners sequester the unwanted molecules as they move along. Several passes of the blood along the pathway might be required to completely remove the specific unwanted molecules.

The flow rate of blood moving through the pathway must be fast enough to prevent coagulation, yet not so fast as to damage the blood cells. Examples of ranges are from about 10 to about 1000 ml of blood per min., preferably between about 50 and about 750 ml/min. and most preferably the flow rate for removal of antibodies using the invention is between about 100 and about 500 ml/min. Heparin can also be added to the blood to prevent coagulation. Processing of an entire host's blood volume (~5 L) would require approximately 2.5 hours to achieve complete removal of antibodies or other undesired molecules from the blood.

The flow can be continuous. Alternatively, the flow can be interrupted to increase the interaction of the unwanted molecules with their immobilized binding partners. Likewise, the shape of the device having the immobilized binding partners can be such that it will encourage some swirling and/or backflow to increase the interaction time between the unwanted molecules and the immobilized binding partners.

Uses

The current invention can be used in reducing organ or tissue transplant rejection by removing specific antibodies against foreign antigens found in the transplanted organ or tissue and providing circulating blood substantially of these antibodies. The invention can also be used as part of a quantitative assay for specific antibodies found in the blood. For example, a whole body assay for the titer of anti-A and anti-B antibodies can be performed. First, the antibodies from the blood can be removed by the filtration described above. Second, the bound antibodies are released by competing with free floating antigens or with other very low ionic strength buffers to prevent binding. Third, released antibodies can be titered using a method such as a hemagglutination assay.

Also, the invention can be used to preparatively purify specific antibodies from the blood without the need to plasmapherese. The steps are similar to the quantification assay described above.

Additionally, the invention can be used to remove excess amounts of antibodies present in the blood.

Further, the invention can be used to identify, quantify and/or remove other molecules having binding partners, such as virions or ligands, from the host's blood.

What is claimed is:

1. A method for reducing the number of unwanted antibodies in a subject's blood, the method comprising:
   a) removing blood from the subject;
   b) passing the blood along an enclosed pathway;
   wherein said pathway comprises one or more semi-permeable hollow fibers with one or more membranes having surfaces positioned substantially perpendicular to the length of the one or more hollow fibers and antigens specific for the unwanted antibodies immobilized on the one or more membranes,
   wherein by passing the blood along the pathway the unwanted antibodies are sequestered by the immobilized antigens, thereby treating the blood; and
   c) returning the treated blood to the internal circulation of said subject,
   wherein the returned treated blood has a reduced number of unwanted antibodies compared to before treatment.

2. The method of claim 1, wherein at least a portion of the enclosed pathway is composed of a material selected from the group consisting of nitrocellulose, cellulose, nylon, plastic, rubber, polyacrylamide, agarose, poly(vinyl alcohol-co-ethylene), and combinations thereof.

3. The method of claim 1, wherein the one or more semi-permeable hollow fibers are at least partially dimpled or twisted to increase mixing of the blood within the one or more hollow fibers, thereby increasing contact of the blood with the immobilized antigens.

4. The method of claim 1, wherein the step of passing the blood through the enclosed pathway comprises continuous or temporarily interrupted passage of the blood through the enclosed pathway.

5. The method of claim 1, wherein antigens specific for the unwanted antibodies are further immobilized on the walls of the semi-permeable hollow fiber.

6. The method of claim 1, wherein a plurality of membranes are provided within the semi-permeable hollow fiber, thereby dividing the length of the hollow fiber into three or more successive sections.

7. The method of claim 6, wherein the enclosed pathway further comprises permeable carrier spheres trapped within successive sections defined by two membranes, wherein the diameter of the spheres is less than the diameter of the hollow fiber, and wherein antigens specific for the unwanted antibodies are further immobilized on the spheres.

8. The method of claim 1, wherein the unwanted antibodies are antibodies associated with a disease state characterized by an excess of antibodies present in the blood.

9. The method of claim 1, wherein the unwanted antibodies are selected from the group consisting of anti-A blood protein antibodies, anti-B blood protein antibodies, anti-protein A antibodies, anti-protein G antibodies and antibodies against major histocompatibility complex molecules.

10. The method of claim 9, wherein the unwanted antibodies are anti-A blood protein antibodies or anti-B blood protein antibodies.

11. The method of claim 1, wherein the antigens are attached to the one or more membranes by a process selected from the group consisting of chemical modification, covalent bonding, strong ionic bonding, hydrogen bonding, and use of a linker.

12. The method of claim 11, wherein the chemical modification is accomplished by treatment with a compound selected from the group consisting of cyanogen bromide, hydrogen peroxide, sodium periodate, epichlorohydrin, 1,4-butanedioldiglycidol ether, cyanuric chloride, carbonyldiimidazole, substituted sulfonyl chloride and fluoromethyl pyridinium salts.

13. The method of claim 1, wherein the antigens are attached to the one or more membranes by avidin or biotin linkers.

14. A method for reducing the number of unwanted antigens in a subject's blood, the method comprising:
   a) removing blood from the subject;
   b) treating said blood by passing the blood along an enclosed pathway;
   wherein said pathway comprises one or more semi-permeable hollow fibers with one or more membranes having surfaces positioned substantially perpendicular to the length of the one or more hollow fibers and antibodies specific for the unwanted antigens immobilized on the one or more membranes,
   wherein by passing the blood along the pathway the unwanted antigens are sequestered by the immobilized antibodies; and
   c) returning the treated blood to the internal circulation of said subject,
   wherein the returned treated blood has a reduced number of unwanted antigens compared to before treatment.

15. The method of claim 14, wherein at least a portion of the enclosed pathway is composed of a material selected from the group consisting of nitrocellulose, cellulose, nylon, plastic, rubber, polyacrylamide, agarose, poly(vinyl alcohol-co-ethylene), and combinations thereof.

16. The method of claim 14, wherein the one or more semi-permeable hollow fibers are at least partially dimpled or twisted to increase mixing of the blood within the one or more hollow fibers, thereby increasing contact of the blood with the immobilized antibodies.

17. The method of claim 14, wherein the step of passing the blood through the enclosed pathway comprises continuous or temporarily interrupted passage of the blood through the enclosed pathway.

18. The method of claim 14, wherein antibodies specific for the unwanted antigens are further immobilized on the walls of the semi-permeable hollow fiber.

19. The method of claim 14, wherein a plurality of membranes are provided within the semi-permeable hollow fiber, thereby dividing the length of the hollow fiber into three or more successive sections.

20. The method of claim 19, wherein the enclosed pathway further comprises permeable carrier spheres trapped within successive sections defined by two membranes, wherein the diameter of the spheres is less than the diameter of the hollow fiber, and wherein antibodies specific for the unwanted antigens are further immobilized on the spheres.

21. The method of claim 14, wherein the antibodies are attached to the one or more membranes by a process selected from the group consisting of chemical modification, covalent bonding, strong ionic bonding, hydrogen bonding, and use of a linker.

22. The method of claim 21, wherein the chemical modification is accomplished by treatment with a compound selected from the group consisting of cyanogen bromide, hydrogen peroxide, sodium periodate, epichlorohydrin, 1,4-butanedioldiglycidol ether, cyanuric chloride, carbonyldiimidazole, substituted sulfonyl chloride and fluoromethyl pyridinium salts.

23. The method of claim 14, wherein the antibodies are attached to the one or more membranes by avidin or biotin linkers.

* * * * *